United States Patent
Quirk (10) Patent No.: US 6,600,057 B2
(45) Date of Patent: Jul. 29, 2003

(54) MATRIX METALLOPROTEINASE INHIBITORS

(75) Inventor: Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 200 days.

(21) Appl. No.: 09/753,140

(22) Filed: Dec. 29, 2000

(65) Prior Publication Data

US 2002/0086877 A1 Jul. 4, 2002

(51) Int. Cl.$^7$ ................................................. C07C 50/12
(52) U.S. Cl. ........................ 552/298; 514/533; 514/569; 514/680
(58) Field of Search .................. 552/298; 514/533, 514/569, 680

(56) References Cited

U.S. PATENT DOCUMENTS

| | | |
|---|---|---|
| 4,613,502 A | 9/1986 | Turková et al. |
| 4,868,108 A | 9/1989 | Bahar et al. |
| 4,876,332 A | 10/1989 | Tsilibary et al. |
| 4,883,760 A | 11/1989 | Heelies |
| 4,904,469 A | 2/1990 | Petereit et al. |
| 4,943,522 A | 7/1990 | Eisinger et al. |
| 4,956,302 A | 9/1990 | Gordon et al. |
| 4,999,285 A | 3/1991 | Stiso |
| 5,037,735 A | 8/1991 | Khanna et al. |
| 5,059,425 A | 10/1991 | Tsilibary et al. |
| 5,112,608 A | 5/1992 | Scott et al. |
| 5,141,850 A | 8/1992 | Cole et al. |
| 5,147,339 A | 9/1992 | Sundström |
| 5,169,754 A | 12/1992 | Siiman et al. |
| 5,188,938 A | 2/1993 | Khanna et al. |
| 5,196,196 A | 3/1993 | Scott et al. |
| 5,236,844 A | 8/1993 | Basset et al. |
| 5,270,168 A | 12/1993 | Grinnell |
| 5,270,447 A | 12/1993 | Liotta et al. |
| 5,275,785 A | 1/1994 | May et al. |
| 5,280,106 A | 1/1994 | Liotta et al. |
| 5,324,634 A | 6/1994 | Zucker |
| 5,332,479 A | 7/1994 | Uenoyama et al. |
| 5,354,447 A | 10/1994 | Uenoyama et al. |
| 5,354,692 A | 10/1994 | Yang et al. |
| 5,372,809 A | 12/1994 | Liotta et al. |
| 5,382,346 A | 1/1995 | Uenoyama et al. |
| 5,389,092 A | 2/1995 | Guillemet et al. |
| 5,415,994 A | 5/1995 | Imrich et al. |
| 5,464,822 A | 11/1995 | Christophers et al. |
| 5,484,726 A | 1/1996 | Basset et al. |
| 5,496,453 A | 3/1996 | Uenoyama et al. |
| 5,516,891 A | 5/1996 | Siwruk et al. |
| 5,541,069 A | 7/1996 | Mortensen et al. |
| 5,559,041 A | 9/1996 | Kang et al. |
| 5,569,608 A | 10/1996 | Sommer |
| 5,585,356 A | 12/1996 | Liotta et al. |
| 5,595,885 A | 1/1997 | Stetler-Stevenson et al. |
| 5,602,040 A | 2/1997 | May et al. |
| 5,605,809 A | 2/1997 | Komoriya et al. |
| 5,622,871 A | 4/1997 | May et al. |
| 5,641,636 A | 6/1997 | Strauss, III et al. |
| 5,656,503 A | 8/1997 | May et al. |
| 5,670,381 A | 9/1997 | Jou et al. |
| 5,698,404 A | 12/1997 | Strauss, III et al. |
| 5,698,671 A | 12/1997 | Stetler-Stevenson et al. |
| 5,710,005 A | 1/1998 | Rittenburg |
| 5,712,172 A | 1/1998 | Huang et al. |
| 5,714,342 A | 2/1998 | Komoriya et al. |
| 5,731,162 A | 3/1998 | Gatti et al. |
| 5,736,341 A | 4/1998 | Sorsa et al. |
| 5,741,659 A | 4/1998 | Ralls et al. |
| 5,766,961 A | 6/1998 | Pawlak et al. |
| 5,770,460 A | 6/1998 | Pawlak et al. |
| 5,770,691 A | 6/1998 | Fields et al. |
| 5,798,273 A | 8/1998 | Shuler et al. |
| 5,804,213 A | 9/1998 | Rolf |
| 5,820,874 A | 10/1998 | Mahoney et al. |
| 5,830,468 A | 11/1998 | Bini |
| 5,834,212 A | 11/1998 | Okada et al. |
| 5,869,277 A | 2/1999 | Stetler-Stevenson et al. |
| 5,876,944 A | 3/1999 | Kuo |
| 5,879,951 A | 3/1999 | Sy |
| 5,895,765 A | 4/1999 | Rheinheimer et al. |
| 5,916,521 A | 6/1999 | Bunce et al. |
| 5,922,322 A | 7/1999 | Bini |
| 5,922,550 A | 7/1999 | Everhart et al. |
| 5,935,796 A | 8/1999 | Fosang |
| 5,939,331 A | 8/1999 | Burd et al. |
| 5,985,675 A | 11/1999 | Charm et al. |
| 5,989,921 A | 11/1999 | Charlton et al. |
| 6,020,181 A | 2/2000 | Bini |

(List continued on next page.)

FOREIGN PATENT DOCUMENTS

| | | |
|---|---|---|
| DE | 4000-797 A | 1/1990 |
| EP | 0 306 772 A1 | 3/1989 |
| EP | 0 398 621 A2 | 11/1990 |
| EP | 0 462 182 B1 | 12/1991 |
| EP | 0 296 724 B1 | 1/1995 |
| EP | 0 833 159 A2 | 4/1998 |
| EP | 0 884 393 A1 | 12/1998 |
| GB | 2 147 206 A | 5/1995 |

(List continued on next page.)

OTHER PUBLICATIONS

Herouy. Y et al Eur. J. Dermatol. Apr.–May 2000: 10(3):173–80.*

J Invest Dermatol. Sep. 2000 115(3):337–44.*

(List continued on next page.)

Primary Examiner—Paul J. Killos
(74) Attorney, Agent, or Firm—Kilpatrick Stockton LLP (57) ABSTRACT

The present invention provides compounds that are effective in treating disorders caused by the enzymatic activity of matrix metalloproteinases. These disorders include, but are not limited to, rheumatoid arthritis, osteoarthritis, periodontal disease, aberrant angiogenesis, tumor invasion and metastasis, corneal ulceration, and in complications of diabetes. The present invention is also is useful for treating wounds.

8 Claims, 4 Drawing Sheets

U.S. PATENT DOCUMENTS

| | | |
|---|---|---|
| 6,022,948 A | 2/2000 | Goldberg |
| 6,025,150 A | 2/2000 | Livant |
| 6,037,137 A | 3/2000 | Komoriya et al. |
| 6,043,087 A | 3/2000 | Bini et al. |
| 6,060,256 A | 5/2000 | Everhart et al. |
| 6,074,869 A | 6/2000 | Pall et al. |
| 6,080,575 A | 6/2000 | Heidtmann et al. |
| 6,093,398 A | 7/2000 | Khaw et al. |
| 6,127,139 A | 10/2000 | Te Koppele et al. |
| 6,136,610 A | 10/2000 | Polito et al. |
| 6,140,068 A | 10/2000 | Livant |
| 6,140,134 A | 10/2000 | Rittenburg |
| 6,143,506 A | 11/2000 | Golub et al. |
| 6,156,271 A | 12/2000 | May |
| 6,166,084 A | 12/2000 | Bloor |
| 6,180,288 B1 | 1/2001 | Everhart et al. |
| 6,183,972 B1 | 2/2001 | Kuo et al. |
| 6,191,255 B1 | 2/2001 | Seiki et al. |
| 6,194,221 B1 | 2/2001 | Rehg et al. |
| 6,203,757 B1 | 3/2001 | Lu et al. |
| 6,221,579 B1 | 4/2001 | Everhart et al. |
| 6,225,127 B1 | 5/2001 | Thompson et al. |
| 6,235,539 B1 | 5/2001 | Carpenter |
| 6,258,548 B1 | 7/2001 | Buck |
| 6,274,703 B1 | 8/2001 | Goldberg |
| 6,280,687 B1 | 8/2001 | Golub et al. |
| 6,294,344 B1 | 9/2001 | O'Brien |
| 6,297,020 B1 | 10/2001 | Brock |

FOREIGN PATENT DOCUMENTS

| | | |
|---|---|---|
| JP | 63210665 A | 9/1988 |
| JP | 04-183397 A2 | 6/1992 |
| JP | 05034353 A | 2/1993 |
| JP | 05-244985 A2 | 9/1993 |
| JP | 06167497 A | 6/1994 |
| JP | 06213888 A | 8/1994 |
| JP | 06300757 A | 10/1994 |
| JP | 07159402 A | 6/1995 |
| JP | 08136548 A | 5/1996 |
| JP | 08201392 A | 8/1996 |
| JP | 08217800 A | 8/1996 |
| JP | 08226918 A | 9/1996 |
| JP | 09087299 A | 3/1997 |
| JP | 09136841 A | 5/1997 |
| JP | 09206099 A | 8/1997 |
| JP | 409249700 A | 9/1997 |
| JP | 10160736 A | 6/1998 |
| JP | 10232189 A | 9/1998 |
| JP | 10287700 A | 10/1998 |
| JP | 10313896 A | 12/1998 |
| JP | 11083858 A | 3/1999 |
| JP | 11318449 A | 3/1999 |
| WO | WO98/29560 | 7/1988 |
| WO | WO90/10062 | 2/1989 |
| WO | WO91/11714 | 1/1990 |
| WO | WO90/10228 | 9/1990 |
| WO | WO90/11287 | 10/1990 |
| WO | WO92/12428 | 1/1991 |
| WO | WO91/12333 | 8/1991 |
| WO | WO92/11021 | 7/1992 |
| WO | WO94/01775 | 7/1992 |
| WO | WO/13874 | 8/1992 |
| WO | WO92/13096 | 8/1992 |
| WO | WO94/10208 | 10/1992 |
| WO | WO95/30903 | 5/1994 |
| WO | WO96/33413 | 4/1995 |
| WO | WO97/06439 | 8/1995 |
| WO | WO98/22800 | 11/1996 |
| WO | WO98/23958 | 11/1996 |
| WO | WO97/00449 | 1/1997 |
| WO | WO97/04080 | 2/1997 |
| WO | WO98/39657 | 6/1997 |
| WO | WO97/25437 | 7/1997 |
| WO | WO98/04287 | 2/1998 |
| WO | WO98/46787 | 4/1998 |
| WO | WO98/40475 | 9/1998 |
| WO | WO00/20860 | 10/1998 |
| WO | WO98/42864 | 10/1998 |
| WO | WO00/31538 | 11/1998 |
| WO | WO99/05261 | 2/1999 |
| WO | WO99/65519 | 12/1999 |
| WO | WO00/02904 | 1/2000 |
| WO | WO00/18805 | 4/2000 |
| WO | WO00/27625 | 5/2000 |
| WO | WO01/10437 A1 | 8/2000 |
| WO | WO00/63700 | 10/2000 |
| WO | WO00/75163 A1 | 12/2000 |
| WO | WO01/04157 A2 | 1/2001 |

OTHER PUBLICATIONS

Hurst et al. "Development and Characterization of a New Polyclonal Antibody Specifically Against Tissue Inhibitor of Metalloproteinases 4 in Human Breast Cancer", Biochem Biophys Res Commun, Feb. 16, 2001, 166–171 281(1), PMID 11178975.

Brassart et al. "Conformational Dependence of Collagenase (Matrix Metalloproteinase–1) Up–Regulation by Elastin Peptides in Cultured Fibroblasts", J Biol Chem, Nov. 17, 2000, PMID 11084020.

Stracke et al. "Biochemical Characterization of the Catalytic Domain of Human Matrix Metalloproteinase 19. Evidence of a Role as a Potent Basement Membrane Degrading Enzyme", J Biol Chem, May 19, 2000; 14809–16, 275(20), PMID 10809722.

Olson et al. "Characterization of the Monomeric and Dimeric Forms of Latent and Active Matrix Metalloproteinase–9. Differential Rates for Activation by Stromelysin 1", J Biol Chem, Jan. 28, 2000, 2661–8, 275(4), PMID 10644727.

Fujise et al. Prognostic Impact of Cathepsin B and Matrix Metalloproteinase–9 in Pulmonary Adenocarcinomas by Immunohistochemical Study, Lung Cancer, Jan. 19–26, 27 (1), PMID 10672780.

Jones et al. "Expression of MMP–2 and MMP–9, Their Inhibitors, and the Activator MT1–MMP in Primary Breast Carcinomas", J Pathol, Oct. 1999, 161–8, 189(2), PMID 10547569.

Ambrose et al. "Detection System for Reaction–Rate Analysis in a Low–Volume Proteinase–Inhibition Assay", Anal Biochem, Oct. 15, 1998, 150–7, 263(2), PMID 9799526.

Baker et al. "Real–time monitoring of recombinant protein concentration in animal cell cultures using an optical biosensor", *Genet. Eng. Biotechnol.* (1997): 17(2&3), 69–74.

Chemical Abstracts 16—Fermentation and Bioindustrial Chemistry, vol. 128, No. 6, 1998, 128:60742q.

Stivers, et al. "A miniaturized self–contained single–use disposable quantitative test for hemoglobin A1c in blood at the point of care", *Diabetes Technol Ther* (2000) Winter:2(4):517–26. PMID: 11469613.

Maliszewska et al. "Development of an ultrasensitive enzyme immunoassay for the determination of matrix metalloproteinases–9 (MMP–9) levels in normal human cerebrospinal fluid", *J. Neuroimmunol* (2001), Jun. 1:116(2):233–7.

Wang et al. "One-step sandwich enzyme immunoassay using monoclonal antibodies for detection of human enamelysin (MMP–20)" *Eur J Oral Sci* Dec. 2000;108(6):530–7. PMID: 11153928.

Hanemaaijer et al. "Increased gelatinase0A and gelatinase–B activities in malignant vs. benign breast tumors" *Intl J Cancer* Apr.15, 2000; 86(2):204–7. PMID: 10738247.

Stearns et al. "Evidence for increased activated metalloproteinase 2 (MMP–2a) expression associated with human prostate cancer progression" *Incol Res* (1996);8(2):69–75. PMID:8859777.

Manicourt et al. "An assay for matrix metalloproteinases and other proteases acting on proteoglycans, casein, or gelatin" *Anal Biochem* Dec. 1993;215(2):171–9. PMID: 8122775.

Cooksley et al. "Immunoassays for the detection of human collagenase, stromelysin, tissue inhibitor of metalloproteinases (TIMP) and enzyme–inhibitor complexes" *Matrix* Oct. (1990);10(5):285–91. PMID: 1964712.

Hoffman et al. "Matrix Metalloproteinases in Human Melanoma" *The Journal of Investigative Dermatology, Inc.* (2000) pp. 337–44.

Trengove et al. "Analysis of the acute and chronic wound environments: the role of proteases and their inhibitors" *Wound Repair and Regeneration,* Nov.–Dec. (1999) pp. 442–52.

Vaalamo et al. "Differential Expression of Tissue Inhibitors of Metalloproteinases (TIMP–1, –2, –3, and –4) in Normal and Aberrant Wound Healing" *Human Pathology* vol. 30, No. 7 (Jul. 1999), pp. 795–802.

Soo et al. "Differential Expression of Matrix Metalloproteinases and Their Tissue–Derived Inhibitors in Cutaneous Wound Repair" *Inhibitor Expression in Wound Repair, Plastic and Reconstruction Surgery* (Feb. 2000), pp. 638–647.

Saarialho–Kere, U.K. "Patterns of matrix metalloproteinases and TIMP expression in chronic ulcers" *Arch Dermatol Res* (1998) 290 (Suppl):S47–S54.

Herouy et al. "Matrix metalloproteinases and venous leg ulceration" *Eur J Dermatol* 2000; 9: 173–80.

Herouy et al. "Matrix metalloproteinases and venous leg ulceration" *Eur J Dermatol* vol. 10, Issue 3, Apr.–May 2000: 173–80, Review article.

Whittaker et al. "Matrix Metalloproteinases and their Inhibitors—Current Status and Future Challenges" *Celltransmissions,* vol. 17, No. 1, pp. 3–14, No date.

Zembower et al. "Novel Anthraquinone Inhibitors of Human Leukocyte Elastase and Cathepsin $G^{1}$" *J. Med. Chem.* 1992, 35, 1597–1605.

Brem et al. "Interstitial chemotherapy with drug polymer implants for the treatment of recurrent gliomas" *J Neurosurg* 1991 74:441–446.

Shaw et al. "Metalloproteinase inhibitors: new opportunities for the treatment of rheumatoid arthritis and osteoarthritis" *Exp. Opin. Invest. Drugs* (2000) 9(7):1469–1478.

Maliszewska et al. "Development of an untrasensitive enzyme immunoassay for the determination of matrix metalloproteinases–9 (MMP–9) levels in normal human cerebrospinal fluid", *J. Neuroimmunol.* (2001): 116(2), 233–238. Chemical Abstracts, 7—Enzymes, vol. 135, No. 16, 135:223205.

Wang et al. "One–step sandwich enzyme immunoassay using monoclonal antibodies for detection of human enamelysin (MMP–20)", *Eur. J. Oral Sci.* (2000): 108(6), 530–537. Chemical Abstracts, 7—Enzymes, vol. 134, No. 11., 134:143641f.

Terstappen, et al. "Methods and reagents for the rapid and efficient isolation of circulating cancer cells using immunomagnetic enrichment combines with flow cytometric and immunocytochemical analysis", *Immunivest: University of Texas Southwestern Medical Center/Dallas, USA.* PCT Int. Appl. WO99 41,613, Aug. 19, 1999, US Appl. PV110,202, Nov. 30, 1998; pp. 115. Chemical Abstracts, 9—Biochemical Methods, vol. 131, No. 12, 1999, 131:155517w.

Harrison et al. "Mechanic Studies on the Human Matrix Metalloproteinase Stromelysin", Biochemistry, Nov. 10, 1992, 10757–62, 31(44), PMID 1420192.

Zucker et al. "Immunoassay of Type IV Collagenase/Gelatinase (MMP–2) in Human Plasma", J Immunol Methods, Apr. 8, 1992, 189–98, 148(1–2), PMID 1373424.

Clark et al. "Polyclonal Antibodies Against Human Fibroblast Collagenase and the Design of an Enzyme–Linked Immunosorbent Assay to Measure TIMP–Collagenase Complex", Matrix, Apr. 1992, 108–15, 12(2), PMID 1318493.

Knight et al. "A Novel Coumarin–Labelled Peptide for Sensitive Continuous Assays of the Matrix Metalloproteinases," FEBS Lett, Jan. 27, 1992, 263–6, 296(3), PMID 1537400.

Angelton et al. "Fluorogenic Peptide Substrates Optimized for Five Human Matrix Metalloproteinases", Matrix Suppl, 1992, 89–90, 1, PMID 1480101.

Stack et al. "Application of N–Carboxyalkyl Peptides to the Inhibition and Affinity Purification of the Porcine Matrix Metalloproteinases Collagenase, Gelatinase, and Stromelysin", Arch biochem Biophys, Sep. 1992, 393, 297(2), PMID 1654808.

Netzel–Arnett et al. "Continuously Recording Fluorescent Assays Optimized for Five Human Matrix Metalloproteinases", Anal Biochem, May 15, 1991, 86–92, 195(1).

Clark et al. "Polyclonal and Monoclonal Antibodies Against Human Tissue Inhibitor of Metalloproteinases (TIMP) and the Design of an Enzyme–Linked Immunosorbent Assay to Measure TIMP", Matrix, Apr. 1991 76–85, 11(2), PMID 1649376.

Brophy et al. "Tissue Inhibitor of Metalloproteases (TIMP) is Matrix Associated in Aortic Tissue: Report of a Radioimmunoassay", Biochem Biophys Res Commun, Mar. 30, 1990, 898–903, 167(3), PMID 2322285.

Teahan et al. "Substrate Specificity of Human Fibroblast Stromelysin. Hydrolysis of Substance P and its Analogues", Biochemistry, Oct. 17, 1989, 8497–501, 28(21), PMID 2481496.

Harrison et al. "A Semicontinuous, High–Performance Liquid Chromatography–Based Assay for Stromelysin", Anal Biochem, Jul. 1989, 110–3, 180 (1), PMID 2479283.

Stetler–Stevenson et al. "The Activation of Human Type IV Collagenase Proenzyme. Sequence Identification of the Major Conversion Product Following Organomercurial Activation", J Biol Chem, Jan. 25, 1989, 264(3), 1353–6, PMID 2536363.

Hoyhtya et al. "Monoclonal Antibodies to Type IV Collagenase Recognize a Protein with Limited Sequence Homology to Interstitial Collagenase and Stromelysin", FEBS Lett, Jun. 6, 1988, 109–13, 233(1), PMID 2838321.

Nwomeh et al. "Dynamics of the Matrix Metalloproteinases MMP-1 and MMP-8 in Acute Open Human Dermal Wounds", Wound Repair Regen, Mar.–Apr. 1998, 127–34, 6(2), PMID 9776855.

Nielsen et al. "Expression of Matrix Metalloprotease–9 in Vascular Pericytes in Human Breast Cancer", Lab Invest, Oct. 1997, 345–55, 77(4), PMID 9354769.

Kodate et al. "Expression of Matrix Metalloproteinase (Gelatinase) in T1 Adenocarcinoma of the Lung", Pathol Int, Jul. 1997, 461–9, 47(7), PMID 97378788.

Itoh et al. Flow Injection Analysis for Measurement of Activity of Matrix Metalloproteinase–7 (MMP–7), J Pharm Biomed Anal, Jun. 1997, 1417–26, 15(9–10), PMID 9226571.

Verheijen et al. "Modified Proenzymes as Artificial Substrates for Proteolytic Enzymes: Colorimetric Assay of Bacterial Collagenase and Matrix Metalloproteinase Activity Using Modified Pro–Urokinase", Biochem J, May 1, 1997, 603–9, 323 (Pt 3)(3), PMID 9169591.

Sang et al. "Activation of Human Progelatinase A by Collagenase and Matrilysin: Activation of Procollagenase by Matrilysin", J Protein Chem, Apr. 1996, 243–53, 15(3), PMID 8804571.

Nagase, et al. "Human Matrix Metalloproteinase Specificity Studies Using Collagen Sequence–Based Synthetic Peptides", Biopolymers, 1996, 399–416, 40(4), PMID 8765610.

McGeehan et al. "Characterization of the Peptide Substrate Specificities of Interstitial Collagenase and 92kDa Gelatinase, Implications for Substrate Optimization", J Biol Chem, Dec. 30, 1994, 32814–20, 269(52), PMID 7806505.

Bickett et al. A High Throughput Fluorogenic Substrate for Stromelysin (MMP–3), Ann NY Acad Sci, Sep. 6, 1994, 351–5, 732, PMID 7978805.

Nagase et al. Design and Characterization of a Fluorgenic Substrate Selectively Hydrolyzed by Stromelysin 1 (Matrix Metalloproteinase–3), J Biol Chem, Aug. 19, 1994, 20952–7, 269(33), PMID 8063713.

Okazaki et al. "Gene Expression of MMPs and TIMPs in the Process of Hepatic Fibrosis" Nippon Rinsho, Feb. 1993, 428–34, 51(2), PMID 8464157.

Niedzwiecki et al. "Substrate Specificity of the Human Matrix Metalloproteinase Stromelysin and the Development of Continuous Fluorometric Assays", Biochemistry, Dec. 22, 1992, 12618–23, 31(50), PMID 1472498.

* cited by examiner wherein R is:

MATRIX METALLOPROTEINASE INHIBITORS

TECHNICAL FIELD

The present invention is directed to compounds and their pharmaceutically acceptable salts, which inhibit matrix metalloproteinases, and are therefore useful in the treatment of mammals having disease-states alleviated by the inhibition of such matrix metalloproteinases.

BACKGROUND OF THE INVENTION

Matrix metalloproteinases ("MMPs)" are a family of proteinases (enzymes) involved in the degradation and remodeling of connective tissues. Members of this family of endopeptidase enzymes are present in various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes, and cartilage. Excessive degradation of extracellular matrix by MMPs is implicated in the pathogenesis of many diseases, includingrheumatoid arthritis, osteoarthritis, periodontal disease, aberrant angiogenesis, tumor invasion and metastasis, corneal ulceration, and in complications of diabetes. Another disorder wherein MMPs play a major role is in chronic wounds. Chronic wounds that are refractive to normal healing processes are characterized by an increase in the activity of matrix metalloproteinases. MMP inhibition is, therefore, recognized as a good target for therapeutic intervention.

In normal tissues, cellular connective tissue synthesis is offset by extracellular matrix degradation, the two opposing effects existing in dynamic equilibrium. Degradation of the matrix is brought about by the action of MMPs released from resident connective tissue cells and invading inflammatory cells. Normally these catabolic enzymes are tightly regulated at the level of their synthesis and secretion and also at the level of their extracellular activity, the latter through the action of specific regulators, such as TIMPs (tissue inhibitors of metalloproteinases), which form inactive complexes with MMPs, and more general proteinase regulators which form complexes with MMPs. These complexes prevent MMP action. Cellular level control of MMP activity occurs primarily by regulating MMP gene expression and by down regulating the expression of the membrane bound MMPs (MT-MMP) that activate the excreted proenzyme form of the MMP.

TIMPs can provide useful treatments for diseases associated with the excessive degradation of extracellular matrix, such as arthritic diseases (rheumatoid arthritis and osteoarthritis), bone resorptive diseases (such as osteoporosis), the enhanced collagen destruction associated with diabetes, periodontal disease, corneal ulceration, ulceration of the skin, tumor invasion and metastasis, and aberrant angiogenesis.

TIMPs are glycoproteins and specifically regulate interstitial collagenases, typically on a 1:1 stoichiometric basis. That is, TIMPs form very specific regulatory complexes with the MMPs, only regulating a specific subset of the MMPs. In chronic wounds, the ratio of MMP to TIMP is high, such that most of the MMPs are unregulated. In fact, with elevated proteinase levels, the TIMP molecules themselves can be hydrolyzed. But there is no naturally occurring TIMP molecule that singly regulates all types of MMPs.

Many disorders are a result of uncontrolled breakdown of connective tissues by MMPs. These problems include, for example, rheumatoid arthritis; osteoarthritis; osteopenias such as osteoporosis, periodontitis, gingivitis, corneal epidermal or gastric ulceration; tumour metastasis, invasion and growth; neuroinflammatory disorders, including those involving myelin degradation, for example multiple sclerosis; and angiogenesis dependent diseases, which include angiofibromas, hemangioma, solid tumors, leukemia, metastasis, telangiectasia psoriasis scleroderma, pyogenic granuloma, *Myocardial angiogenesis*, plaque neovascularization, cororany collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. Another major disorder that results from abnormal regulation of MMPs is chronic wounds.

One major reason that chronic wounds do not heal is that MMPs destroy the newly formed wound bed. However, the accelerated, uncontrolled breakdown of connective tissues by MMP catalysed resorption of the ECM is a feature of acute or chronic non-healing skin wounds. Many individuals suffer from these types of wounds. Open cutaneous wounds represent one major category of such wounds and include burn wounds, neuropathic ulcers, pressure sores, venous stasis ulcers, and diabetic ulcers. Worldwide, eight million people have chronic leg ulcers and seven million people have pressure sores (Clinica 559, 14–17, 1993). In the U.S. alone, the prevalence of skin ulcers is 4.5 million, including two million pressure sore patients, 900,000 venous ulcer patients and 1.6 million diabetic ulcer patients (Med Pro Month, June 1992, 91–94). The cost involved in treating these wounds is staggering and, at an average of $3,000 per patient, reaches over $13 billion per year for the U.S. alone.

Burn wounds have a reported incidence of 7.8 million cases per year worldwide, 0.8 million of which need hospitalization (Clinica 559). In the U.S., there are 2.5 million burn patients per year, 100,000 of which need hospitalization and 20,000 of which have burns involving more than 20% of the total body surface area (MedPro Month, June 1992).

Thus, there is a need in the art for improved regulation of MMPs to promote healing of chronic and acute wounds. It is necessary to have an inhibitor with relatively good affinity yet which is selective so not to be toxic to the cells. Furthermore, there is a need in the art to control overactive MMPs.

SUMMARY OF THE INVENTION

The invention provides new compounds which are useful as inhibitors of matrix metalloproteinases and which are effective in treating disease-states characterized by excessive activity of matrix metalloproteinases. Accordingly, one aspect of the invention is directed to 4,5-dihydroxyanthaquinone-2-carboxylic acid (AQCA) and derivatives thereof. 4,5-dihydroxyanthaquinone-2-carboxylic acid has the following formula:

As one embodiment of the present invention, it has been found that AQCA is an inhibitor of matrix metalloproteinases. In addition, derivatives of AQCA have been found to be highly effective inhibitors of metalloproteinases. For example, modification at the 2 position of the AQCA yields a wide variety of effective matrix metalloproteinase inhibitors. Thus, the present invention comprises the use of AQCA as a matrix metalloproteinase and also comprises AQCA molecules that have been modified at the 2 position. A preferred method of modifying the AQCA molecule is by addition to the carboxyl group at the 2 position.

The AQCA molecule and the derivatives of the AQCA molecules are effective matrix metalloproteinase inhibitors and can be used as a therapeutic agent for those disorders wherein metalloproteinases are a factor in the etiology of the disorder. For example, the use of the present invention in treating wounds is particularly useful. The matrix metalloproteinase of the present invention can be administered by topical, transdermal, oral, rectal or parenteral (e.g., intravenous, subcutaneous or intramuscular) route.

These and other features and advantages of the present invention will become apparent after a review of the following detailed description of the disclosed embodiments and the appended claims.

DETAILED DESCRIPTION OF THE INVENTION

As used herein, the term "Pharmaceutically acceptable salt" refers to those salts which retain the biological effectiveness and properties of the free bases or free acids and which are not biologically or otherwise undesirable. If the compound exists as a free base, the desired salt may be prepared by methods known to those of ordinary skill in the art, such as treatment of the compound with an inorganic acids such as hydrochloric acid, hydrobromic acid, sulfuric acid, nitric acid, phosphoric acid and the like; or with an organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. If the compound exists as a free acid, the desired salt may also be prepared by methods known to those of ordinary skill in the art, such as the treatment of the compound with an inorganic base or an organic base. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The term "mammal" includes humans and all domestic and wild animals, including, without limitation, cattle, horses, swine, sheep, goats, dogs, cats, and the like.

The phrase "therapeutically effective amount" refers to that amount of a compound of the present invention which, when administered to a mammal in need thereof, is sufficient to effect treatment, as defined below, for disease-states alleviated by the inhibition of matrix metalloproteinase activity, such as the activity of stromelysin, gelatinase, matrilysin and/or collagenase. (Please see Saarialho-Kere UK. Patterns of matrix metalloproteinase and TIMP expression in chronic ulcers. Arch Dermatol Res. 1998 Jul;290 Suppl:S47–54; Herouy Y, Trefzer D, Zimpfer U, Schopf E, Wanscheidt W, Norgauer J. Matrix metalloproteinases and venous leg ulceration. Eur J Dermatol. 2000 Apr–May;10 (3):173–80; Shaw T, Nixon J S, Bottomley K M. Metalloproteinase inhibitors: new opportunities for the treatment of rheumatoid arthritis and osteoarthritis. Expert Opin Investig Drugs. 2000 Jul;9(7):1469–78.; Hofmann U B, Westphal J R, Van Muijen G N, Ruiter D J; Matrix metalloproteinases in human melanoma. J Invest Dermatol. 2000 Sep;115(3):337–44). The amount of a compound of the present invention which constitutes a "therapeutically effective amount" will vary depending on the compound, the disease-state and its severity, and the mammal to be treated, but can be determined routinely by one of ordinary skill in the art having regard to his own knowledge and to this disclosure.

The terms "treating" or "treatment" as used herein cover the treatment of a disease-state in a mammal, particularly in a human, which disease-state is alleviated by the inhibition of matrix metalloproteinase activity, such as the activity of stromelysin, gelatinase, matrilysin and/or collagenase, and include:

(i) preventing the disease-state from occurring in a mammal, in particular, when such mammal is predisposed to the disease-state but has not yet been diagnosed as having it;

(ii) inhibiting the disease-state, i.e., arresting its development; or (iii) relieving the disease-state, i.e., causing regression of the disease-state.

"Stereoisomers" refers to compounds having identical molecular formulae and nature or sequence of bonding but differing in the arrangement of their atoms in space.

Many of the compounds of the present invention, or their pharmaceutically acceptable salts, have at least two asymmetric carbon atoms in their structure, and may therefore exist as single stereoisomers, racemates, and as mixtures of enantiomers and diastereomers. All such single stereoisomers, racemates and mixtures thereof are intended to be within the scope of this invention.

The compounds of the present invention inhibit mammalian matrix metalloproteinases, such as the stromelysins, gelatinases, matrilysin and collagenases, and are therefore useful for treating diseases associated with the MMP-induced excessive degradation of matrix and connective tissue within the mammal, for example, arthritic diseases (rheumatoid arthritis and osteoarthritis), bone resorptive diseases (such as osteoporosis), the enhanced collagen destruction associated with diabetes, periodontal disease, corneal ulceration, ulceration of the skin, tumor invasion and metastasis, and aberrant angiogenesis.

Chronic wounds that are refractive to normal healing processes are characterized by an increase in the activity of matrix metalloproteinases. These enzymes are responsible for their continued degradation, and therefore the continued turnover, of newly formed basal extracellular matrix (ECM). The normal formation of this matrix marks a committed entry into the healing process. Thus, this inability to heal is a hallmark of chronic wounds. MMPs include the collagenases, stromilysins, and gelatinases; all of which are found in be chronic wound microenvironment. Normally these enzymes are prevented from destroying the ECM by the action of four tissue inhibitors of metalloproteinases (TIMPs 1–4). In chronic wounds, the ratio of MMP to TIMP is high, such that most of the MMPs are uninhibited. (Please see Soo C, Shaw WW, Zhang X, Longaker M T, Howard E W, Ting K. Differential expression of matrix metalloproteinases and their tissue-derived inhibitors in cutaneous wound repair. *Plast Reconstr Surg*. 2000 Feb;105(2):638–47.; Trengove N.J., Stacey M C, MacAuley S, Bennett N, Gibson J, Burslem F, Murphy G, Schultz G. Analysis of the acute and chronic wound environments: the role of proteinases and their inhibitors. Wound Repair Regen. 1999 Nov–Dec;7(6):442–52.; Vaalamo M, Leivo T, Saarialho-Kere U. Differential expression of tissue inhibitors of metalloproteinases (TIMP-1, -2, -3, and -4) in normal and aberrant wound healing. *Hum Pathol*. 1999 Jul;30(7):795–802).

In fact, with elevated proteinase levels, the TIMP molecules themselves can be hydrolyzed. In contrast, acute wounds (which heal well) are characterized by overall lower MMP levels and by lower MMP to TIMP ratios. Paradoxically, MMP function (albeit at a lower level) is required to reorganize the ECM during healing, and can actually promote new cell migration into the wound site. It is therefore desirable to maintain some basal level of MMP activity. One of the ways in which healing may be promoted in chronic wounds is to lower the level of MMP activity, but not to fully inhibit the activity. The present invention includes the synthesis and use of a novel MMP inhibitor series. The present invention allows for the manipulation of MMP enzymatic activity in the wound bed.

Figure 1:
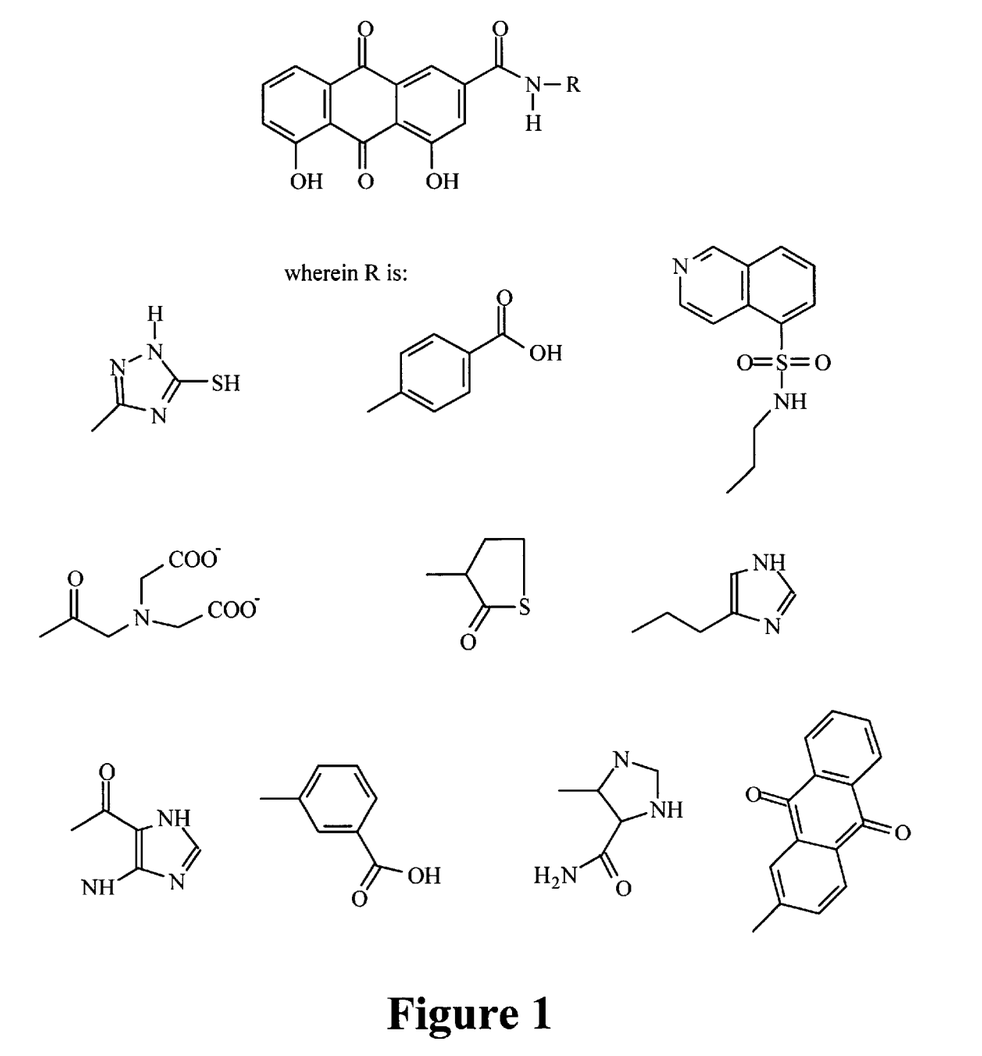
FIG. 1 shows several examples of derivatives of AQCA.

The present invention includes the use of the molecule 4,5-dihydroxyanthraquinone-2-carboxylic acid (AQCA) as a matrix metalloproteinases inhibitor and as a therapeutic agent for treating disorders that are associated with matrix metalloproteinase activity. The present invention also includes derivatives of the AQCA molecule, especially AQCA molecules that have been modified at the 2 position. In particular, the carboxylate moiety at the 2 position of the AQCA molecule can be modified by treatment with EDC/NHS in order to make the functional reactive against a primary amine. The general reaction is outlined as follows:

The carboxyl group at the 2 position of the AQCA can therefore be coupled to any primary amine. Examples of derivatives of AQCA that have been modified at the 2 position carboxyl group are shown in FIG. 1. AQCA was resuspended in water/20% DMSO to a final concentration of 100 mM. The pH was adjusted to 7.0 by the addition of dilute base or acid as required. Mercaptoethylamine (or alanine hydroxamate) was dissolved in a small amount of DMSO followed by the slow addition of water until the compound was at a concentration of 150 mM. To the AQCA solution was added N-hydroxysuccinimide (NHS), to a final concentration of 175 mM and N-ethyl-N'-(dimethylaminopropyl)-carbodiimide (EDC) to a final concentration of 400 mM The solution was incubated at 37° C. with gentle stirring for 30 minutes. The previously prepared mercaptoethylamine (or alanine hydroxamate) solution was added to this reaction slowly over a period of 5 minutes. Stirring continued for an additional 30 minutes. The final solution was inactivated by the addition of ethanolamine-HCl to a final concentration of 1.0 M. The final mixture was taken to dryness in a rotovac over a period of 10 hours. The solid material was then resuspended in 500 μL of water/10% DMSO and the coupled compound was purified away from unreacted species via RP-HPLC. A 250 mm×100 mm 5μ Hypersil ODS-2 RP column was chromatographed with a mobile phase of: A: 0.1% TFA/water, B: 0.1% TFA/acetronitrile. After sample injection, a gradient of 100%A (0 to 2 min) and 0–60% B (2 to 25 min) was applied. The compound was detected at 450 nm and was 96% pure by peak integration. The eluting peak was pooled, was mixed with 3 volumes of water, and was lyophilized. The compound was aliquoted and stored frozen at −20° C.

A particularly desirable AQCA derivative is anthraquinyl-mercaptoethyamine shown in the following structure:

Another preferred AQCA derivative is anthraquinylalanine hydroxamate shown in the following structure:

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J Neurosurg.* 74:441–446 (1991).

The dosage of the compound will depend on the condition being treated, the particular compound, and other clinical factors such as weight and condition of the human or animal and the route of administration of the compound. It is to be understood that the present invention has application for both human and veterinary use. For topical administration to humans, a dosage of between approximately 0.01 to 10 mg/mL, preferably between approximately 0.05 and 5 mg/mL, and most preferably between approximately 0.1 to 1 mg/mL, is generally sufficient.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and a pharmaceutically acceptable carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A topical delivery system includes a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

The present invention is further described by the examples which follow. Such examples, however, are not to be construed as limiting in any way either the spirit or scope of the present invention. In the examples, all parts are parts by weight unless stated otherwise.

EXAMPLE 1

Two enzymatic assays were performed.

The first assay measures the enzymatic hydrolysis of fluoresceinated collagen by MMP-9 as a function of time. Fluoresceinated collagen (Molecular Probes, Inc.), at a concentration of 5 μM was added to reaction buffer (50 mM Tris-HCl (pH 7.6), 150 mM NaCl, 5 mM $CaCl_2$, 0.1 mM $NaN_3$) and was placed into a Spectrosil quartz fluorometer cuvette. MMP at a concentration of 0.1 μM was mixed with varying amounts of compound and incubated at 25° C. for 10 minutes in order to effect binding. The protein mixture was added to the collagen substrate, and was quickly mixed. Fluorescence emission intensity at 520 nm was measured as a function of time (excitation wavelength 495 nm) in a Shimadzu RF5301 fluorometer. The fluorescein release assay was used to determine the inhibitory constant ($K_i$) of the compound inhibitor ([I]) according to Segel (1993) via the use of Dixon plots (1/v vs. [I]), such that:

$$\text{slope}=K_m/(V_{max}K_i[S]) \quad (1)$$

where $K_m$ is the Michaelis constant, $V_{max}$ is the reaction maximum velocity, and [S] is the substrate concentration.

The second assay utilized the technique of fluorescence resonance energy transfer (FRET). The substrate peptide (Calbiochem) comprised seven amino acids coupled to a carboxyl terminal dinitrophenyl acceptor, and an amino terminal 2-aminobenzo-anthraniloyl (Abz) moiety donor. Cleavage of this substrate by MMP-9 results in the liberation of a fluorescent product (365 nm excitation, 450 nm emission). Compound at a concentration of 1 μM was added to reaction buffer (50 mM Tris- HCl (pH 7.6), 150 mM NaCl, 5 mM $CaCl_2$, 0.1 mM $NaN_3$) and was placed into a black 96-well microtiter plate well that had been previously blocked with 1% BSA. MMP at a concentration of 0.5 μM was mixed with varying amounts of compound and incubated at 25° C. for 10 minutes in order to effect binding. The protein mixture was added to the peptide substrate, and was quickly mixed. Fluorescence intensity as a function of time was measured with a Dynex MFX fluorescence microtiter plate reader. Fluorescence intensity was related back to moles of peptide cleaved by producing a standard curve with an Abz containing non-FRET peptide. Inhibitory constants were derived from the curves as above. (Segel, IH. (1993) Enzyme Kinetics: Behavior and analysis of rapid equilibrium and steady-state enzyme systems. Wiley Classics Library, John Wiley and Sons, Inc. New York.)

EXAMPLE 2

Figure 2:
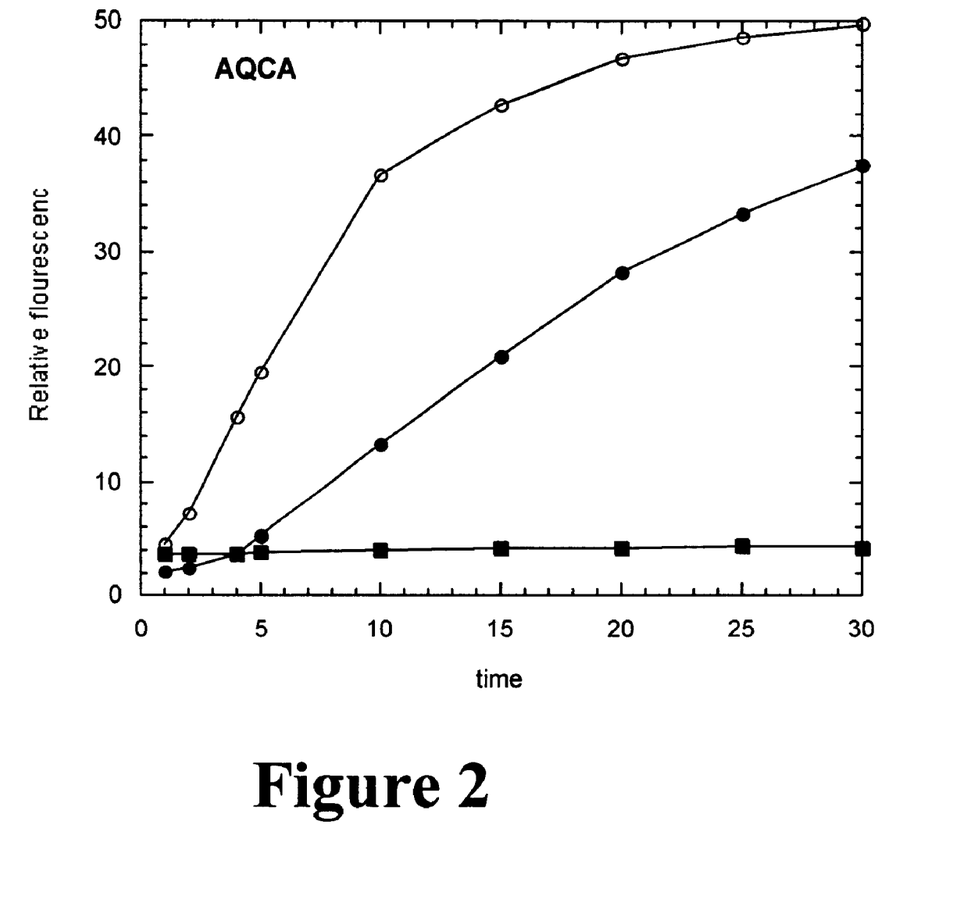
FIG. 2 shows the results of a fluorometric assay showing the inhibitory effect of AQCA on MMP-9.

The inhibition of MMP-9 by AQCA was measured by fluorometric assay. The fluorometric assay measures the cleavage of a fluorogenic peptide substrate (excitation wavelength 355 nm, emission wavelength 455 nm). MMP-9 is incubated with 0 mM AQCA (open circles), 1 mM AQCA (closed circles); or 2 mM AQCA (closed squares) for 30 minutes at room temperature. Fluorescence is measured at the times (in minutes) indicated.

As shown in FIG. 2, the AQCA inhibited the enzymatic activity of MMP-9 in a dose dependent manner. Inhibition of MMP-9. Fluorometric assay which measures the cleavage of a fluorogenic peptide substrate (excitation wavelength 355 nm, emission wavelength 455 nm). MMP-9 is incubated with 0 mM AQCA (open circles), 1 mM AQCA (closed circles), or 2 mM AQCA (closed squares) for 30 minutes at room temperature. Fluorescence is measured at the times (in minutes) indicated.

EXAMPLE 3

Figure 3:
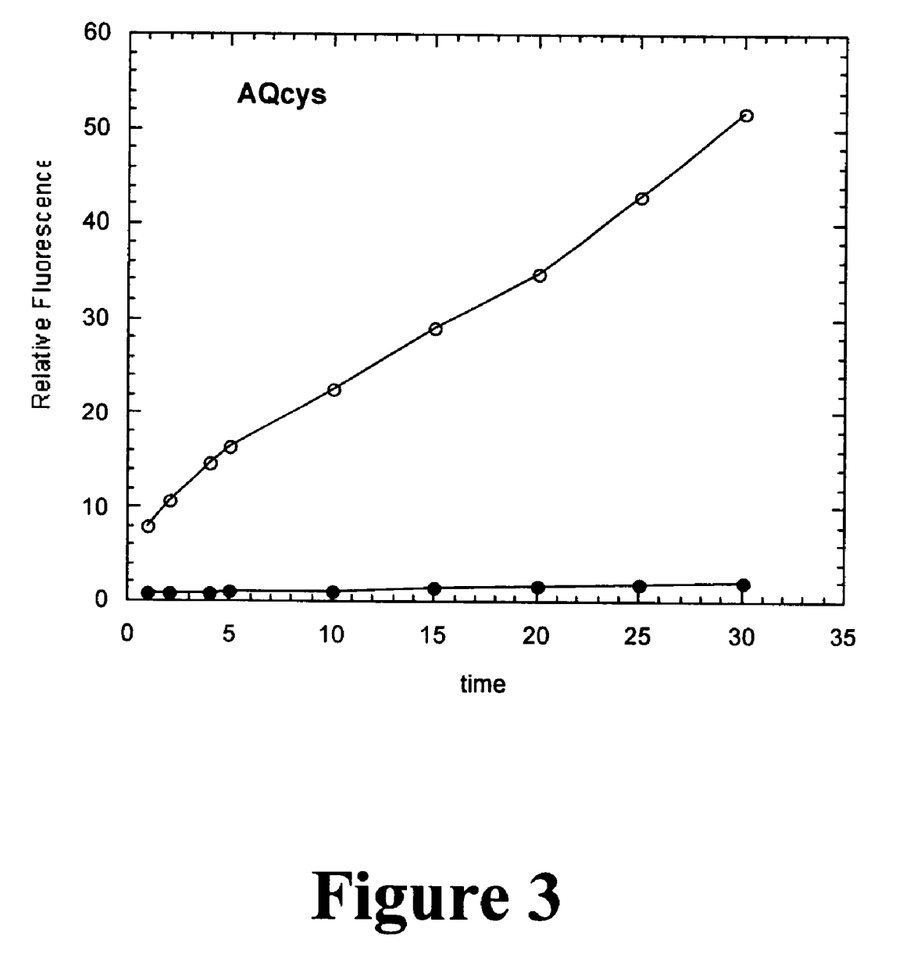
FIG. 3 shows the results of a fluorometric assay showing the inhibitory effect of anthraquinyl-mercaptoethylamine on MMP-9.

The inhibition of MMP-9 by anthraquinyl-mercaptoethylamine was measured by fluorometric assay. The fluorometric assay measures the cleavage of a fluorogenic peptide substrate (excitation wavelength 355 nm, emission wavelength 455 nm). MMP-9 is incubated with 0 mM anthraquinyl mercaptoethylamine (open circles) or 0.25 mM anthraquinyl mercaptoethylamine (closed circles) for 30 minutes at room temperature. Fluorescence is measured at the times (in minutes) indicated.

As shown in FIG. 3, the anthraquinyl mercaptoethylamine inhibited the enzymatic activity of MMP-9.

EXAMPLE 4

Figure 4:
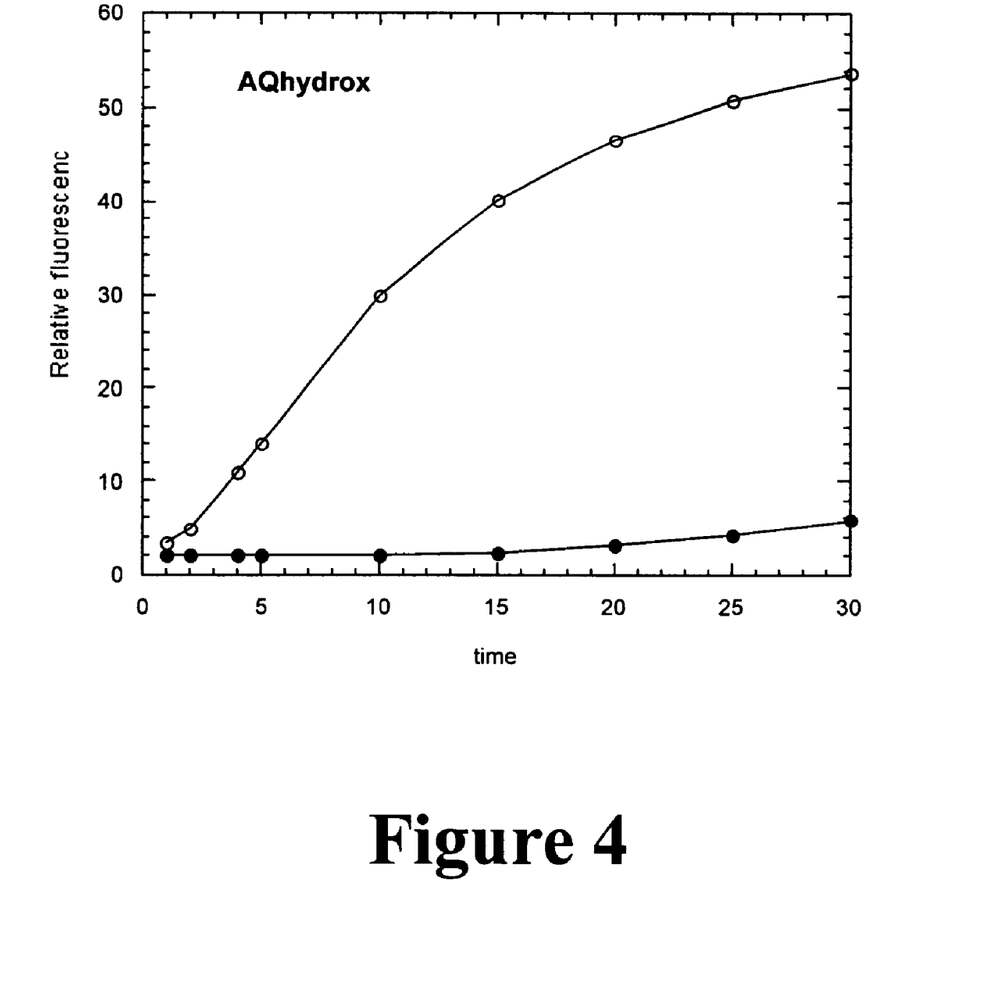
FIG. 4 shows the results of a fluorometric assay showing the inhibitory effect of anthraquinyl-alanine hydroxamate on MMP-9.

The inhibition of MMP-9 by anthraquinyl alanine hyroxamate was measured by fluorometric assay. The fluorometric assay measures the cleavage of a fluorogenic peptide substrate (excitation wavelength 355 nm, emission wavelength 455 nm). MMP-9 is incubated with 0 mM anthraquinyl alanine hyroxamate (open circles) or 0.25 mM anthraquinyl alanine hyroxamate (closed circles) for 30 minutes at room temperature. Fluorescence is measured at the times (in minutes) indicated.

As shown in FIG. 4, the anthraquinyl alanine hyroxamate inhibited the enzymatic activity of MMP-9.

EXAMPLE 5

Viability Assays:

The relative toxicity of the chelating and the substrate peptides was assayed using the skin model Epiderm from MatTek Corp. The individual skin sample containers were preincubated in culture medium at 37° C., 5% $CO_2$ for two hours prior to the addition of the peptide constructs. The sample containers were transferred to 6 well plates that contained fresh media. All peptides were dissolved in PBS at a final concentration of 10 mM, and 100 μL each peptide solution was pipetted onto the surface of the Epiderm sample container. Incubation was continued for 12 hours at 37° C., 5% $CO_2$. After the incubation period, the sample containers were washed three times with PBS and the sample containers were transferred to a 24 well plate that contained 300 μL of MTT assay media per well (MTT concentration was 1 mg/mL). The calorimetric assay was allowed to develop for three hours (incubation at 37° C., 5% $CO_2$). Sample containers were then transferred to a 24 well culture plate that contained 2 mL of isopropanol per well. Extraction of the colored precipitate occurred over a period of four hours at room temperature. Absorbance readings were taken at 570 nm and 650 nm for each sample. The percent viability of each sample relative to a PBS control was calculated as:

$$100 \times (OD_{570}^{sam} - OD_{650}^{sam}) / (OD_{570}^{con} - OD_{650}^{con}) \quad (5)$$

Routinely, each peptide sample was assayed in duplicate or triplicate.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of treating a disorder in a patient wherein the disorder is associated with matrix metalloproteinase comprising administering to the patient a therapeutically effective amount of dihydroxyanthaquinone-2-carboxylic acid or a derivative of dihydroxyanthaquinone-2-carboxylic acid.

2. The method of claim 1, wherein the dihydroxyanthaquinone-2-carboxylic acid or a derivative of dihydroxyanthaquinone-2-carboxylic acid is administered via oral, rectal, ophthalmic, intravitreal, intracameral. nasal, topical, buccal, sublingual, vaginal, parenteral, subcutaneous, intramuscular, intravenous, intradermal, intratracheal, or epidural routes.

3. The method of claim 1, wherein the disorder is a rheumatoid arthritis; osteoarthritis; osteopenias such as osteoporosis, periodontitis, gingivitis, corneal epidermal or gastric ulceration; tumour metastasis, invasion and growth; neuroinflammatory disorders, including those involving myelin degradation, for example multiple sclerosis; and angiogenesis dependent diseases, which include angiofibromas, hemangioma, solid tumors, leukemia, metastasis, telangiectasia psoriasis scleroderma, pyogenic granuloma, *Myocardial angiogenesis*, plaque neovascularization, cororany collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, or placentation.

4. The method of claim 1, wherein the disorder is a wound.

5. The method of claim 1, wherein the derivative of dihydroxyanthaquinone-2-carboxylic acid has the following formula:

wherein R is:

6. The method of claim 1, wherein the derivative of dihydroxyanthaquinone-2-carboxylic acid is anthraquinyl-mercaptoethyamine.

7. The method of claim 1, wherein the derivative of dihydroxyanthaquinone-2-carboxylic acid is anthraquinyl-alanine hydroxamate.

8. The method of claim 1, wherein the dihydroxyanthaquinone-2-carboxylic acid or a derivative of dihydroxyanthaquinone-2-carboxylic acid is administered to the patient topically.

* * * * *